US008353194B2

(12) United States Patent
Reichel

(10) Patent No.: US 8,353,194 B2
(45) Date of Patent: Jan. 15, 2013

(54) INDIRECT DETERMINATION OF THE WASTE GAS RATE FOR METALLURGICAL PROCESS

(75) Inventor: Johann Reichel, Düsseldorf (DE)

(73) Assignee: SMS Siemag AG, Dusseldorf (DE)

( * ) Notice: Subject to any disclaimer, the term of this patent is extended or adjusted under 35 U.S.C. 154(b) by 387 days.

(21) Appl. No.: 12/676,089

(22) PCT Filed: Aug. 8, 2008

(86) PCT No.: PCT/DE2008/001336

§ 371 (c)(1),
(2), (4) Date: Mar. 2, 2010

(87) PCT Pub. No.: WO2009/030192

PCT Pub. Date: Mar. 12, 2009

(65) Prior Publication Data

US 2010/0192672 A1 Aug. 5, 2010

(30) Foreign Application Priority Data

Sep. 7, 2007 (DE) ........................ 10 2007 044 568

(51) Int. Cl.
*G01N 33/20* (2006.01)

(52) U.S. Cl. ...................................................... 73/19.07

(58) Field of Classification Search ................. 73/19.07, 73/861.04, 861.05, 861.06

See application file for complete search history.

(56) References Cited

U.S. PATENT DOCUMENTS

| | | | | | |
|---|---|---|---|---|---|
| 3,188,180 | A | * | 6/1965 | Holler | 204/164 |
| 3,400,585 | A | | 9/1968 | Kraus et al. | |
| 3,520,657 | A | * | 7/1970 | Frumerman | 436/56 |
| 3,522,035 | A | * | 7/1970 | Putman | 75/385 |
| 3,934,470 | A | * | 1/1976 | Amati et al. | 73/861.04 |
| 4,040,789 | A | * | 8/1977 | Voss et al. | 436/114 |
| 4,251,269 | A | | 2/1981 | Hoshi et al. | |
| 4,251,270 | A | | 2/1981 | Hoshi et al. | |
| 4,273,312 | A | | 6/1981 | Phillips et al. | |
| 4,305,906 | A | * | 12/1981 | Mikasa et al. | 422/62 |
| 5,518,931 | A | * | 5/1996 | Plessers | 436/52 |

FOREIGN PATENT DOCUMENTS

| | | |
|---|---|---|
| DE | 28 39 316 | 3/1979 |
| WO | EP2005006848 | 2/2006 |

* cited by examiner

*Primary Examiner* — Lisa Caputo
*Assistant Examiner* — Punam Roy
(74) *Attorney, Agent, or Firm* — Cozen O'Connor

(57) ABSTRACT

A method for the indirect determination of the waste gas rate in metallurgical processes. A reference gas such as helium is first added to the waste gas, specifically at a time which, with respect to flow, sufficiently precedes the taking of a sample such that a thorough mixing of the reference gas and waste gas is carried out, i.e., a virtually homogeneous distribution is achieved, and a quantitative helium analysis and nitrogen analysis of the waste gas, measured by a mass spectrometer, is carried out while taking into account the added amount of helium.

3 Claims, 1 Drawing Sheet

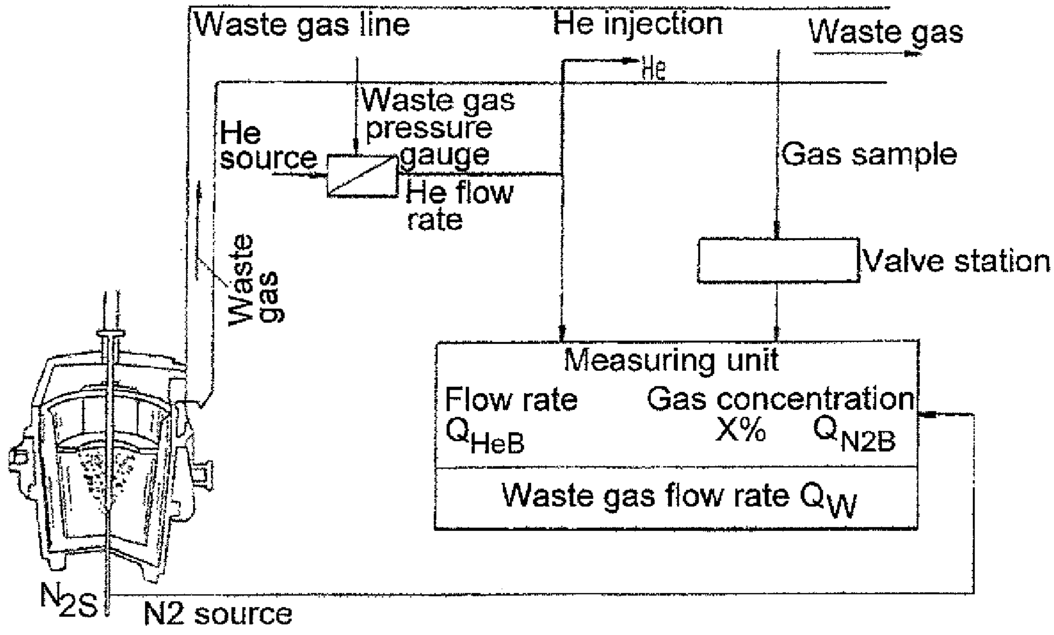
Waste gas line
He injection
Waste gas
He
Waste gas pressure gauge
He source
Gas sample
He flow rate
Valve station
Waste gas
Measuring unit
Flow rate
Gas concentration
$Q_{HeB}$
X%
$Q_{N2B}$
Waste gas flow rate $Q_W$
$N_{2S}$
N2 source

INDIRECT DETERMINATION OF THE WASTE GAS RATE FOR METALLURGICAL PROCESS

PRIORITY CLAIM

This is a U.S. national stage of application No. PCT/DE2008/001336, filed on Aug. 8, 2008, which claims Priority to the German Application No.: 10 2007 044 568.9, filed: Sep. 7, 2007, the contents of both being incorporated herein by reference.

BACKGROUND OF THE INVENTION

1. Field of the Invention

The invention relates to the indirect determination of the waste gas rate or waste gas flow rate in metallurgical processes.

2. Prior Art

Information about the waste gas, its time-dependent composition and/or amount, is important for controlling metallurgical processes.

PCT/EP2005/006848 discloses a method for noncontacting waste gas measurement, particularly at a converter, wherein a segment of the waste gas volume is measured by means of an FTIR spectrometer.

In another method known from DE 28 39 316, a mass-spectrometric monitoring of a sample is carried out on the ionization currents for selected peaks relating to CO, $CO_2$, $N_2$ and a reference gas in the sample. The reference gas can be helium, for example.

SUMMARY OF THE INVENTION

It is an object of the invention to provide a method by which the waste gas rate in metallurgical processes can be indicated more precisely.

According to one embodiment of the invention, a reference gas such as helium is first added to the waste gas, specifically at a time which, with respect to flow, sufficiently precedes the taking of a sample such that a thorough mixing of the reference gas and waste gas is carried out, i.e., a virtually homogeneous distribution is achieved.

The indirect determination of the waste gas rate based on helium then consists in the helium analysis and nitrogen analysis of the waste gas measured by a mass spectrometer while taking into account the added amount of helium.

Combining the two affords the possibility of calculating the waste gas rate by the following formula:

$$Q_W = \frac{1}{He} Q_{HeB} + \frac{He_{Air}}{He} Q_L, \tag{1}$$

where:

$Q_W$ is the calculated waste gas rate $Nm^3$/min;

$Q_{HeB}$ is the measured helium flow rate $Nm^3$/min;

$Q_L$ is the calculated infiltrated air $Nm^3$/min;

He is the measured helium concentration in the waste gas (–); and $He_{Air}$ is the measured concentration in the air (–), corresponding to 5.2 ppm.

The infiltrated air can be determined by the following formula:

$$Q_L = \frac{\frac{N_2}{He}}{N_{2Air} - \frac{N_2}{He} He_{Air}} Q_{HeB} - \frac{1}{N_{2Air} - \frac{N_2}{He} He_{Air}} Q_{N2S}, \tag{2}$$

$$\text{where } Q_{N2S} = Q_{N2B} + Q_{N2Steel} \tag{3}$$

and $N_2$, He is the measured waste gas nitrogen, helium concentration;

$N_{2Air}$, $He_{Air}$ is the nitrogen, helium concentration in the air corresponding in absolute values to 0.78 and 5.2 E-4;

$Q_{N2S}$ is the source nitrogen quantity $Nm^3$/min;

$Q_{N2B}$ is the measured nitrogen rate (process gas) $Nm^3$/min; and $Q_{N2Steel}$ is the calculated nitrogen rate as degassing product $Nm^3$/min.

When formulas (2) and (3) are inserted into formula (1), the waste gas rate can be put into the following form:

$$Q_W = \frac{1}{He - \frac{N_2}{N_{2Air}} He_{Air}} Q_{HeB} - \frac{1}{He \frac{N_{2Air}}{He_{Air}} - N_2} (Q_{N2B} + Q_{N2Steel}) \tag{4}$$

The negative component of the formula describes the effect of the oxygen ($Q_{N2B}$) blown into the liquid steel in case of a special steel treatment and the nitrogen rate in the degassing ($Q_{N2Steel}$) of the liquid steel on the globally calculated waste gas rate.

Under normal circumstances, argon is used as stirring gas or inert gas so that only the amount of nitrogen occurring during degassing has theoretical significance for the accuracy of the waste gas flow rate calculation. Since this is very low compared to the global waste gas rate, it can be ignored.

Waste gas rate determined by a measuring unit (mass spectrometer) in $Nm^3$/min: Simplified formula:

$$Q_W = \frac{1}{He - He_{Air} \frac{N_2}{N_{2Air}}} Q_{HeB} \tag{5}$$

Estimation of the necessary minimum helium concentration in the waste gas at which a carbon balance can be achieved with an accuracy of +/−(0.005-0.007%):

Approximately $100 \times He_{Air}$

BRIEF DESCRIPTION OF THE DRAWINGS

FIG. 1 is a schematic representation of a system for the indirect determination of waste gas rate according to one embodiment of the present invention.

DETAILED DESCRIPTION OF THE DRAWINGS

FIG. 1 is the measurement system described above applied in the control of a metallurgical process, specifically by way of the example of a Vacuum Oxygen Decarburization (VOD) process. Only the parts necessary for understanding the invention are shown in the drawing.

Helium from another source is injected into the waste gas flow. The amount is adjusted corresponding to the waste gas pressure. The helium source, the waste gas pressure gauge, and the helium flow regulator are preferably arranged and shown in FIG. 1.

The corresponding value for the added amount of helium is acquired by the measuring unit and is used for the calculation.

A sample is then removed from the waste gas flow and supplied to the measurement station.

The waste gas flow rate $Q_W$ is then determined according to the formula described above from the flow rate $Q_{HeB}$, the gas concentration X %, the quantity of $N_2$ process gas $Q_{N2B}$, and taking into account the quantity of $N_2$ reaction gas $Q_{N2steel}$ if required for measuring accuracy.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for the indirect determination of a waste gas rate of a waste gas in a metallurgical process, comprising:

adding helium as a reference gas to the waste gas;

measuring a helium flow rate;

mixing the reference gas and the waste gas such that a substantially homogeneous distribution is achieved;

taking a sample of the mixed reference gas and waste gas; and analyzing the sample by a mass spectrometer to perform a reference gas analysis and nitrogen analysis of the waste gas, while taking into account the added amount of the reference gas, wherein the waste gas rate is determined by the formula:

$$Q_W = \frac{1}{He - He_{Air}\frac{N_2}{N_{2Air}}} Q_{HeB},$$

where $Q_W$ is the calculated waste gas rate $Nm^3/min$;

$N_2$, He are respective waste gas nitrogen, helium concentrations;

$N_{2Air}$, $H_{Air}$ are nitrogen, helium concentrations in air; and $Q_{HeB}$ is the measured helium flow rate $Nm^3/min$.

2. The method according to claim 1, wherein adding the reference gas further comprises regulating a flow rate of the helium at a helium gas source.

3. The method according to claim 1, further comprising determining concentrations of $O_2$, CO, $CO_2$, Ar, and $H_2$ in the sample gas by mass spectrometry.

* * * * *